United States Patent [19]

Babior

[11] Patent Number: 4,639,373
[45] Date of Patent: Jan. 27, 1987

[54] STABILIZATION OF GRANULOCYTES

[75] Inventor: Bernard M. Babior, Lexington, Mass.

[73] Assignee: New England Medical Center Hospitals, Inc., Boston, Mass.

[21] Appl. No.: 758,514

[22] Filed: Jul. 24, 1985

Related U.S. Application Data

[63] Continuation-in-part of Ser. No. 676,071, Nov. 29, 1984.

[51] Int. Cl.$^4$ .............................................. A61K 35/14
[52] U.S. Cl. .......................................... 424/101; 435/2
[58] Field of Search ............................. 424/101; 435/2

[56] References Cited

PUBLICATIONS

Wille—Chem. Abst., vol. 82, (1975), p. 130 K.
Packham et al—Chem. Abst., vol. 70, (1969), p. 113043e.
Kotelba-Witkowska et al., Transfusion, vol. 22, 121 ff, (1982).
Tullis, Blood, vol. 6, 772–773, (1951).
Crowley et al., Transfusion, vol. 14, 574–580, (1974).
Contreras et al., Cryobiology, vol. 17, 243–251, (1980).
Contreras et al., Transfusion, vol. 18, 46–53, (1978).
Price et al., Transfusion, vol. 25, 238–241, (1985).
Sher et al., Immunology, vol. 31, 337–341, (1976).

*Primary Examiner*—Sam Rosen

[57] ABSTRACT

Granulocytes are effectively preserved during storage for long periods of time without freezing by using as the storage medium a non-toxic buffer containing both gelatin and plasma.

5 Claims, No Drawings

STABILIZATION OF GRANULOCYTES

This application is a continuation-in-part of U.S. Ser. No. 676,071 filed Nov. 29, 1984.

This invention relates to the stabilization or preservation of human leukocytes, particularly granulocytes, and pertains more specifically to the storage of such cells at temperatures above freezing in a non-toxic physiologically acceptable medium containing plasma and gelatin as essential ingredients. After storage in such a medium, the cells substantially display most of their original physiological properties and are of use in the treatment of diseases characterized by a qualitative or quantitative deficiency of these cells.

Although there has been an extensive development of blood banks for collecting human blood and separating it into several different components such as red cells, white cells including neutrophils, platelets, and serum, the maximum physiological or therapeutic use of the components can be made only if they are capable of being stored until needed and/or transported to the place of need. Certain components such as red blood cells and serum can be stored for long periods after freezing under certain conditions, then reconstituted for use. Limited storage of platelets is possible, but they lose their ability to function after at most five days of storage at temperatures above freezing; and the freezing of platelets for storage, though feasible (Kotelba-Witkowska et al., Transfusion, Vol. 22, 121 ff. (1982) is an expensive and little used technique. Neutrophils, on the other hand, have been subject to agglutination or clumping after storage for as little as 48 hours at temperatures above freezing and so have had to be used within two days of preparation; storage of neutrophils by freezing has met with no success.

It has been proposed in Tullis, Blood, Vol. 6, 772–773 (1951) to employ an isotonic buffer containing gelatin together with EDTA, ascorbic acid, sodium acetate and phenol red indicator as a storge medium for leukocytes. Crowley et al., Transfusion, Vol. 14, 574–580 (1974) described decantation of leukocyte-rich plasma from whole blood drawn in buffer containing 0.4% gelatin based on the total blood-buffer composition and stored at 4° C. with or without the addition of various supplements but function of the granulocytes declined markedly after storage for a week. Contreras et al., Cryobiology, Vol. 17, 243–251 (1980) described storage of granulocytes in various plasma-containing storage media at 4° C. but unsatisfactory decline in functionality occurred after 4 days. Contreras et al., Transfusion, Vol. 18, 46–53 (1978) described storage of granulocytes in media containing either plasma or acid-modified gelatin at 4° C. or 22° C. with extensive loss of cells after 3 days. Price et al., Transfusion, Vol. 25, 238–241 (1985) described the use of acid-modified fluid gelatin as a red cell sedimenting agent in the collection of granulocytes but no storage of the granulocytes occurred prior to testing. Sher et al., Immunology, Vol. 31, 337–341 (1976) described use of gelatin as a red cell sedimenting aid in the collection of granulocytes, but the gelatin was washed from the granulocytes before suspending them in an incubation medium with no extended storage.

It has now been found that granulocytes can be effectively stabilized for storage at temperatures below 25° C., preferably below 8° C. over extensive periods of time of at least five days or even seven days or more provided they are suspended in a suitable buffer, one which is non-toxic and physiologically acceptable, containing gelatin and human plasma dissolved therein. After storage, the granulocytes can be transfused without further processing except for warming to a temperature no higher than 40° C. to liquefy any gel which is present; or the granulocytes can be reconstituted for use simply by washing out the gelatin and plasma with buffer which can be the same as or different from the buffer used for storage, or by removal of the gelatin-containing buffer by centrifugation followed by resuspending the granulocytes in a desired buffer or medium.

The buffer employed can be any conventional non-toxic buffer which provides a pH in the desired range. The pH of the buffer may vary over a wide range, from about pH 6.1 to about pH 8.5; preferably the pH is maintained near the neutral point, e.g. about 6.5 to about 7.5 in order to optimally preserve function. For best results, the granulocytes in plasma- and gelatin-containing buffer should be stored at low temperature, e.g. below 8° C., although they may be stored at higher temperatures up to about 25° C. for at least 12 hours with satisfactory results.

Gelatin from any of the usual commercial sources can be used in the practice of the present invention. The amount of gelatin may vary over a wide range, depending in part on the length of storage desired. As little as 1.0% by weight based on the total weight of the total buffer-plasma composition is effective for short storage; there is no critical upper limit on the amount used, except that it must be low enough so that the composition is a liquid, rather than a gel, at a temperature no higher than 40° C. in order to facilitate removal of the gelatin after storage.

The concentration or number of the granulocytes in the buffer may vary over a limited range, from $10^7$ to $10^9$ per ml, preferably from $1 \times 10^8$ to $5 \times 10^8$ per ml.

The plasma employed can be normal human plasma or autologous plasma. The amount of plasma may vary from 25% by weight of the total composition to as much as 90% by weight.

A local anesthetic such as lidocaine is an optional additive which aids in maintaining the cell count at a high level. Other local anesthetics which can be used include procaine, mepivacaine, bupivacaine, and the like.

Tests have shown that granulocytes which have been stored for five days or even seen days or more in accordance with the present invention, then reconstituted by 25-fold dilution of the gelatin and plasma, largely retain all of the desired physiological properties and are substantially free from agglutination or clumping. In particular, they are capable of ingesting and killing opsonized microorganisms.

The following specific examples are intended to illustrate more fully the nature of the present invention without acting as a limitation upon its scope.

In each of the following examples, granulocytes were prepared from freshly drawn human blood which had been anticoagulated by the addition of 15–18% by volume of an acidic and hypertonic buffer, an aqueous solution containing sodium citrate and citric acid (0.38M in citrate and citric acid and 20 mg/ml of glucose at pH 4.8) (ACD). The granulocytes were separated by dextran sedimentation and centrifugation as described in Curnutte et al., J. Clin. Invest., Vol. 53, pp. 1662–1672 (1974). They were then washed in Dulbecco's phosphate buffered saline without calcium or magnesium (PBS) and without removing red cells by hypotonic lysis.

The granulocytes were then suspended in the neutral histidine buffer used as the storage medium: 0.1M sodium citrate, 0.05M histidine, 0.1M glucose, 0.05M sodium pyruvate, and 1 μM lidocaine adjusted to pH 7.4 (HCP).

Autologous human plasma was drawn in the same HCP buffer, 10 ml of blood being mixed with 1.4 ml buffer and spun for 10 minutes successively at 1500 and 2000 rpm respectively with separation of the plasma fraction after each centrifugation.

The following compositions were then prepared, the proportions of gelatin and plasma being expressed as a percentage by weight of the total:

| Composition No. | Gelatin % | Plasma % | Lidocaine (μM) |
|---|---|---|---|
| 1 | 2 | 44 | 0.5 |
| 2 | 1 | 44 | 0.5 |
| 3 | 0.5 | 0 | 0.5 |
| 4 | 0 | 0 | 0.5 |
| 5 | 0 | 44 | 0 |
| 6 | 0.5 | 44 | 0 |
| 7 | 1 | 0 | 0 |
| 8 | 2 | 0 | 0 |

In each case the concentration of granulocytes was $2 \times 10^8$ per ml. and the pH was 7.4 at room temperature.

Five specimens of each of the compositions were stored in a refrigerator at 4° C.

After storage for 7 days at 4° C., each specimen was allowed to warm to room temperature; those specimens which were gels at 4° C. liquified upon warming. The specimens were diluted tenfold with Dulbecco's phosphate-buffered saline without calcium and magnesium. Granulocyte function was then evaluated. Survival of granulocytes was measured by cell count, expressed as a percentage of the initial cell count before storage. Viability was determined by the percentage of cells which excluded Trypan blue when suspended at 0.4% by weight in PBS buffer without calcium and magnesium. Capability of bacterial killing was measured with respect to *S. aureus* using substantially the same procedure as described by Babior et al. in Leukocyte Function, Cline ed., pp. 1–38 (NY 1981).

The results were as follows (average of five specimens):

| Composition No. | Cell Count % initial | Viability % | Bacterial killing % |
|---|---|---|---|
| 1 | 109 | 74 | 98 |
| 2 | 62 | 59 | 95 |
| 3 | 18 | 13 | 74 |
| 4 | 31 | 30 | 69 |
| 5 | 32 | 18 | 99 |
| 6 | 22 | 27 | 96 |
| 7 | 58 | 60 | 57 |
| 8 | 71 | 73 | 73 |

From the foregoing results it is clear that cell counts, viability, and bacterial killing capacity are all preserved to a much greater extent in the compositions containing gelatin and plasma in combination, whereas two or even all three functions are greatly reduced when one or both of these ingredients are omitted.

What is claimed is:

1. The method of stabilizing for storage without freezing human granulocytes obtained from blood which comprises suspending them in a non-toxic buffer containing gelatin and plasma in which the amount of said gelatin is at least 1% by weight of the total composition and less than the amount required to cause said composition to set to a gel at 40° C. or higher and the amount of said plasma is from 25 to 90% by weight of the total composition.

2. The method as claimed in claim 1 including the additional step of storing said suspension without freezing at a temperature below 25° C. for a period of at least five days.

3. The method as claimed in claim 2 in which storing is carried out at a temperature below 8° C.

4. The method of claim 2 in which the pH of the buffer is from 6.1 to 8.0, the storing is carried out at a temperature below 8° C., and the number of granulocytes in said suspension is from $1 \times 10^7$ to $2 \times 10^8$ per ml.

5. A composition comprising granulocytes suspended in a non-toxic buffer at pH 6.1 to 8.0 containing gelatin and plasma, the amount of said gelatin is at least 1% by weight of the total composition and less than the amount required to cause said composition to set to a gel at 40° C. or higher and the amount of said plasma is from 25 to 90% by weight of the total composition.

* * * * *